US006628388B2

(12) United States Patent
Darrow et al.

(10) Patent No.: US 6,628,388 B2
(45) Date of Patent: Sep. 30, 2003

(54) DETECTION OF BIREFRINGENT MICROCRYSTALS IN BILE

(75) Inventors: Chris Darrow, Pleasanton, CA (US); Andrew Mirhej, San Francisco, CA (US); Tino Seger, Berlin (DE)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/815,087

(22) Filed: Mar. 21, 2001

(65) Prior Publication Data

US 2002/0135766 A1 Sep. 26, 2002

Related U.S. Application Data

(60) Provisional application No. 60/246,294, filed on Nov. 7, 2000.

(51) Int. Cl.[7] .................................................. G01J 4/00
(52) U.S. Cl. .................. 356/364; 356/336; 356/338; 356/365; 356/436; 356/440
(58) Field of Search ........................... 356/364, 365, 356/336, 338, 436, 440; 250/225

(56) References Cited

U.S. PATENT DOCUMENTS

| | | | | |
|---|---|---|---|---|
| 3,856,408 A | * | 12/1974 | Hill et al. .................... 356/365 |
| 3,902,805 A | * | 9/1975 | Redner ........................ 356/365 |
| 4,266,874 A | * | 5/1981 | Janin et al. .................. 356/365 |
| 4,912,059 A | * | 3/1990 | Newman et al. ............. 356/364 |
| 6,097,488 A | * | 8/2000 | Grek et al. .................. 356/364 |
| 6,157,448 A | * | 12/2000 | Kowa et al. ................ 356/365 |

* cited by examiner

Primary Examiner—Michael G. Lee
Assistant Examiner—Ahshik Kim
(74) Attorney, Agent, or Firm—Alan H. Thompson; James S. Tak; James M. Skorich

(57) ABSTRACT

A transparent flow channel fluidly communicates a fluid source and a collection reservoir. A light beam passes through a first polarizer having a first plane of polarization. The flow channel is orthogonal to the light beam. The light beam passes through a fluid sample as it flows through the flow channel. The light beam is then filtered through a second polarizer having a second plane of polarization rotated 90° from the first plane of polarization. The birefringence of certain crystalline materials present in the fluid sample rotates the plane of polarization of the light beam. The presence of these microcrystals thus causes a component of the beam to pass through the second polarizer and impinge an electronic photo-detector located in the path of the beam. The photo-detector signals the presence of the microcrystals by generating voltage pulses. A display device visually presents the quantitative results of the assay.

29 Claims, 1 Drawing Sheet

DETECTION OF BIREFRINGENT MICROCRYSTALS IN BILE

This application claims priority from Provisional Patent Application Serial No. 60/246,294, entitled "An Apparatus for Detecting Birefringent Microcrystals in Bile," filed Nov. 7, 2000, and incorporated herein by reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

Acute pancreatitis is a condition that affects over 200,000 persons annually in the United States. It is characterized by inflammation of the pancreas and severe abdominal pain. In extreme cases the illness can lead to renal and respiratory failure and even death. About 20% of all acute pancreatitis patients are considered idiopathic, that is, there is no known cause for the condition. Up to 75% of the idiopathic pancreatitis cases are associated with the presence of microcalculi, also known as microlithiasis, in the common bile duct. These are small stones believed to cause pancreatitis by transiently blocking the pancreatic duct that empties into the duodenum at the sphincter of Oddi.

To diagnose microlithiasis, patients typically undergo endoscopic retrograde cholangiopancreatography ("ERCP") by a gastroenterologist. In this procedure, the patient is sedated, and an endoscope is introduced orally and maneuvered through the stomach to the duodenum at the exit point of the common bile duct. A catheter is introduced into the bile duct through a working channel of the endoscope, and a sample of bile is aspirated from the patient. The patient is then discharged from the hospital and the bile sample is subsequently analyzed by laboratory personnel using a polarization microscope.

The presence of microlithiasis in the bile sample usually requires the pancreatitis patient to undergo further interventional treatment. The preferred treatment is usually a sphincterotomy, an endoscopic procedure in which a cut is made in the sphincter of Oddi to disrupt the sphincter and allow continual drainage of the bile duct. A sphincterotomy in cases of pancreatitis associated with microlithiasis has been shown to reduce the incidence of recurrent pancreatitis from 73% in the absence of a sphincterotomy, to 10% when the procedure has been performed. A sphincterotomy is preferable to the more invasive, involved and costly cholecystectomy, i.e., the surgical excision of the gall bladder.

A disadvantage of the above-described delayed analysis procedure is that the sphincterotomy must be accomplished through a second ERCP after the test result indicating the presence of microlithiasis becomes available. This additional procedure increases the cost of treating the condition and, for a second time, subjects the patient to the inherent risks associated with undergoing ERCP. If the gastroenterologist had knowledge of the presence of microlithiasis at the time of the first ERCP when a bile sample was collected, a sphincterotomy could be performed during the initial ERCP. A device that could make a rapid, intra-operative determination of the presence of microlithiasis could significantly reduce the medical expense when a sphincterotomy is called for.

The protocol for laboratory evaluation of bile for cholesterol microlithiasis varies among medical institutions, although a widely accepted standard is polarized-light microscopy. An example of the foregoing protocol for bile analysis is provided in Cynthia W. Ko, John H. Sekijima, M.D., and Sum P. Lee, M. D., Ph. D., "Billiary Sludge," Annals of Internal Medicine, Vol. 130 (1999), pp. 301–311. Bile is aspirated endoscopically from the patient after the administration of cholecystokinie ("CCK"). The CCK stimulates contraction of the gall bladder and relaxation of the sphincter of Oddi, thereby causing bile to flow out of the gall bladder, through the bile duct, and into the duodenum, where 2 to 5 milliliters of duodenal fluid, including bile, is collected. The sample is placed in a centrifuge tube and spun at 3000 g for 15 minutes.

Several microliters of sediment, suspended in a drop of distilled water, are transferred to a glass slide and examined by polarizing microscopy. When examined in this manner, cholesterol monohydrate crystals appear as bright, rhomboid-shaped plates or clumps of plates against a dark background. Ko et al. regard a positive test as finding more than two crystals of any type in a 100× magnified field or more than four crystals per sample.

The accuracy of the test results been called into question due to a lack of consensus in the medical community regarding the proper temperature at which the bile sample should be maintained prior to microscopic analysis. Some experts contend that cooling to this temperature inhibits bacterial growth during the unavoidable interval between drawing the sample and conducting the assay, while others maintain that cooling artificially induces the formation of precipitates that were not present in the sample in vivo. The accuracy of the test results thus depends whether the sample was cooled, and whether cooling ensures accuracy or is actually inimical to it.

In view of the foregoing, it can be seen that a need exists to provide a device that allows attending medical personnel to test for the presence of microlithiasis in bile during ERCP. More particularly, there is a need for a device that provides for relatively immediate microcrystal detection in bile extracted from a living organism. Such a device would allow the assay to be performed under known, controlled, and near life-like conditions during a period when further interventional treatment, i.e., sphincterotomy, could be immediately administered. Performing the assay immediately after the bile sample is withdrawn from the patient would moot the controversy over whether the bile sample should be cooled to inhibit bacterial growth, or whether such cooling in fact compromises the accuracy of the assay by inducing microcrystal precipitation in the sample.

Furthermore, having the results of an assay immediately available to the attending physician during ERCP would allow the physician, if warranted by the assay results, to immediately proceed with the administration of further interventional treatment. Since the diagnosis and treatment would be performed during the same ERCP, the patient would avoid the risks and discomfort associated with a second ERCP.

As may be seen from the foregoing, there presently exists a need in the art to rapidly detect crystalline materials in a fluid sample, e.g., bile, withdrawn from a patient undergoing ERCP, and thereby overcome the shortcomings, disadvantages and limitations of the prior art. The present invention fulfills this need in the art.

SUMMARY OF THE INVENTION

Briefly, the present invention is an apparatus and method for rapidly detecting crystalline materials such as cholesterol microcrystals in a fluid sample, e.g., a bile sample, withdrawn from a patient undergoing ERCP. The fluid sample flows through a transparent flow channel and into a collection reservoir. An interrogating light beam is polarized by an optical polarizer into a well-defined first plane of polarization. The transparent flow channel is situated orthogonal to the polarized interrogating light beam. The polarized light beam passes through the fluid sample as it flows through the flow channel. The light beam is then directed to a second polarizer that passes only light having a plane of polarization that has undergone some degree of rotation relative to the first plane of polarization.

The birefringence of crystalline materials, such as microcrystalline cholesterol of times contained in the bile of patients suffering from pancreatitus, rotates the plane of polarization of the polarized light beam as it passes through the sample fluid. The presence of such microcrystals thus causes a portion of the interrogating beam to pass through the second polarizer and impinge an electronic photo-detector located in the path of the beam. The electronic photo-detector signals the detection of birefringent microcrystals by generating voltage pulses.

The device rapidly displays the quantitative results of the assay. The microcrystal detection apparatus can be further configured to bar-code scan a patient's medical record number; find, retrieve and print out the designated medical record; and enter the record together with the results of the microcrystal detection test directly into a hospital's patient database via a built-in network interface.

These and other features, aspects and advantages of the present invention will become better understood with reference to the following drawings, description and claims.

DETAILED DESCRIPTION OF THE INVENTION

Figure 1:
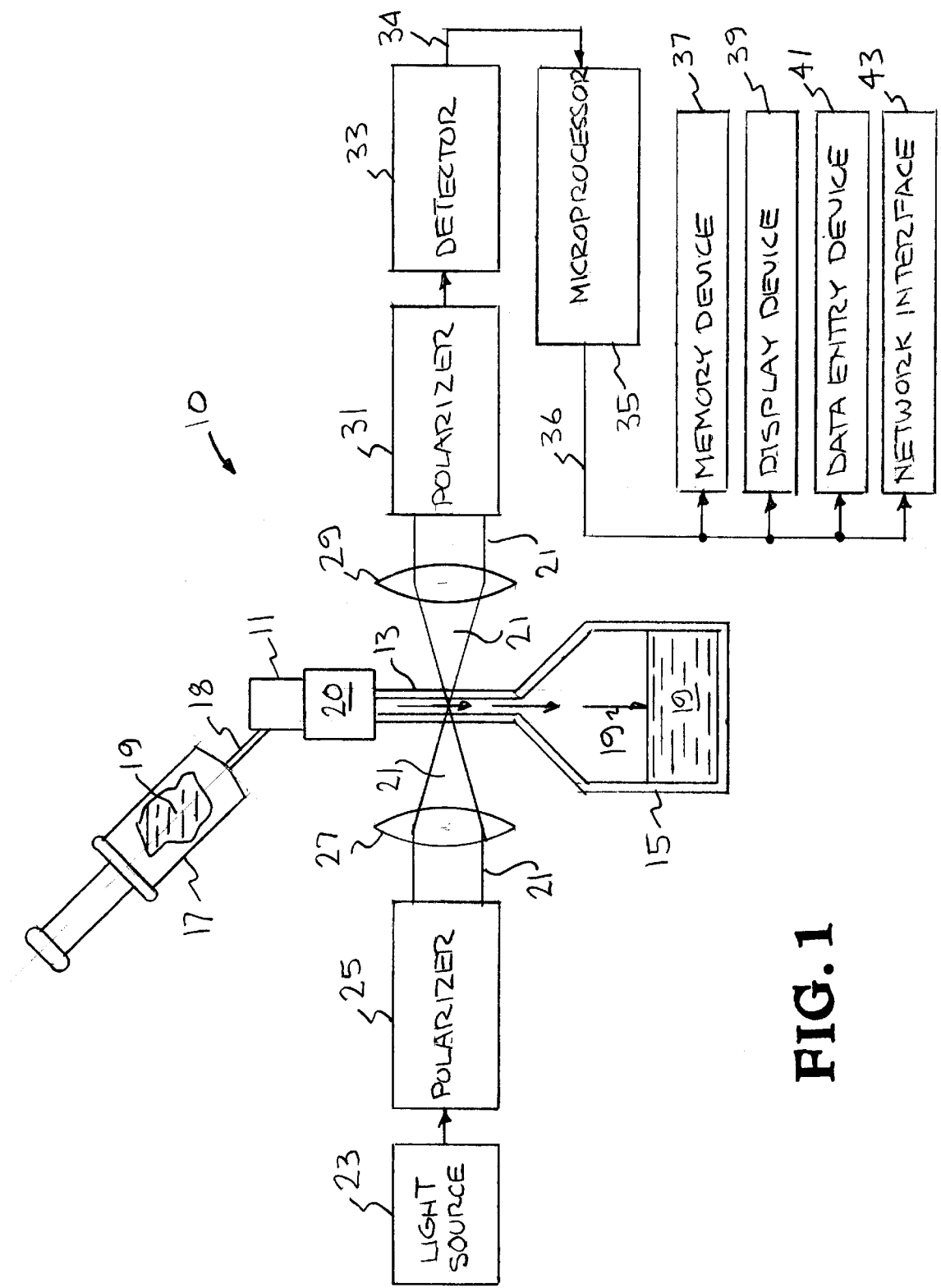
FIG. 1 is a schematic drawing depicting an embodiment of the microcrystal detection device of the present invention, and particularly describing the optics and data processing elements.

The apparatus of the invention is usually used in conjunction with an ERCP of a sedated patient. It allows attending medical personnel to detect the presence or ascertain the absence of birefringent microcrystals, e.g., cholesterol, in a patient's bile within a brief period after the removal and assay of the bile sample so that, if called for, the attending gastroenterologist can proceed with a sphincterotomy in conjunction with the ERCP while the patient is still sedated. For example, the assay results would almost always be known in less than five minutes, often in less than two minutes, and many times in less than one minute.

Turning to the drawings, FIG. 1 schematically illustrates test apparatus 10, an embodiment of the invention including intake fitting 11, tubular flow channel 13, and collection reservoir 15. Flow channel 13 is transparent. A suitable fluid dispensing means, for example, syringe 17, is used to collect fluid 19, e.g., bile, from a patient and inject fluid 19 into and through intake fitting 11. Intake fitting 11 is a "Luer" type fitting that provides a sealed, fluid-tight connection between syringe 17 and flow channel 13 when tip 18 of syringe 17 is inserted therein, and incorporates one-way check valve 20 that allows fluid 19 to enter flow channel 13, but prevents it from escaping. Operation of syringe 17 forces fluid 19 through flow channel 13 and into collection reservoir 15. The direction of flow of fluid 19 is thus parallel to the axial centerline of flow channel 13.

Interrogating light beam 21 is a beam of light emitted by light source 23, and is preferably directed orthogonal to the direction of flow of fluid 19. Beam 21 is passed through polarizer 25, creating a light beam with a well-defined polarization orientation. Beam 21, after being polarized, passes through focusing lens 27 that focuses beam 21 into a relatively small focal region lying within the inner lateral cross-section defined by the inner walls of flow channel 13. After emerging from flow channel 13, beam 21 then passes through collector lens 29, which collects and relays it to polarizer 31. Polarizer 31 passes only light having a plane of polarization that is rotated 90° relative to the plane of polarization of the light passing through polarizer 25. Thus, polarizer 31 blocks light that has retained the original polarization that was selected by polarizer 25. Any portion of beam 21 passing through polarizer 31 impinges electronic photo-detector 33.

In the absence of birefringent microcrystals in fluid 19, virtually no light passes through polarizer 31 because polarizer 31 rejects the polarized light in beam 21 that passed through polarizer 25 and that passed through fluid 19 in flow channel 13 without further rotation. However, when a birefringent crystalline material, e.g., microlithiasis, passes through the focal region of beam 21, a small fraction of the incident light is intercepted by and passes through the crystalline material, emerging from flow channel 13 with a resultant polarization that is rotated from its original plane of polarization. Only the portion of light in beam 21 having a plane of polarization rotated 90° from its plane of polarization on entering flow channel 13 can pass through polarizer 31 and impinge electronic photo-detector 33.

Thus, passage of the crystalline material through beam 21 causes electronic photo-detector 33 to generate electronic signals 34. Each of signals 34 is comprised of a voltage pulse of a duration corresponding to the period that the moving crystalline material lies within the focal region of beam 21. Signals 34 are input into microprocessor 35, which is appropriately programmed to accept or reject each of signals 34 on the basis of its amplitude or duration, or its amplitude and duration.

After all of fluid 19 has flowed through flow channel 13, the final microcrystal count, as represented by processed signal data 36, is input into and recorded by memory device 37, and presented in numerical or graphic form on display device 39. Thus, test apparatus 10 provides an estimate of the total number of microcrystals of a detectable size present per unit volume of fluid 19. The accuracy of the device can be periodically checked by performing an assay on a test sample composed of a calibration solution containing a known concentration of insoluble birefringent microcrystals.

Processed signal data 36 may also be combined with data entered through the data entry device 41 and routed over a network using network interface 43. Data entry device 41 allows patient-specific data, e.g., bar-coded patient identification and date information, to be attached to the assay data file. Network interface 43 transmits the assay results to a database, e.g., a hospital patient database.

In addition to functions associated with collection, processing and routing of data, microprocessor 35 could also be programmed to control the assay procedure. For example, an electrical connection between an appropriately programmed microprocessor 35 and a fluid pump connected to syringe 17 could automatically command the pumping of fluid 19 through flow channel 13 at the appropriate time in the assay cycle.

The f-number of focusing lens 27 (equal to a lens' focal length divided by its diameter) is selected to ensure that its focal region covers most of the inner lateral cross section of flow channel 13. If the focal region of focusing lens 27 is too small, a significant part of flow channel 13 would lie outside the focal region, and thus a substantial portion of fluid 19 would not be examined. This would adversely affect the accuracy of the assay. The f-number of collector lens 29 is selected to ensure that beam 21 exiting the focal region is relayed to polarizer 31 and electronic photo-detector 33 without unnecessary losses.

If the microcrystal count is sufficiently high, the number of undetected microcrystals, e.g., microcrystals passing outside of the focal region, can be statistically estimated within a reasonable certainty. When an even more accurate determination of the degree of microlithiasis is desired, the flow column of fluid 19 can be hydrodynamically focused in flow channel 13 to ensure complete overlap of the focal region of beam 21 and the flow column. Various light sources can be employed. Solid-state devices such as light emitting diodes ("LEDs") and visible-wavelength diode lasers provide superior reliability, cost savings and simplicity, although LEDs typically require a more elaborate focusing lens 27 to achieve a satisfactory focal region within flow channel 13. Diode lasers can be efficiently focused and therefore provide effective signal levels. Additional alternatives include exotic lasers as well as incandescent, electroluminescent and gas-discharge sources.

It should be understood, of course, that the foregoing description relates to a preferred embodiment of the invention and that modifications may be made without departing from the spirit and scope of the invention as set forth in the following claims.

The invention claimed is:

1. A microcrystal detection apparatus comprising:
    a transparent flow channel capable of receiving and flowing a fluid test sample therethrough at substantially the same temperature as when extracted from a patient;
    a first polarizing means for polarizing light into a first plane of polarization;
    a second polarizing means for polarizing light into a second plane of polarization;
    said second plane of polarization being rotated relative to said first plane of polarization; and
    a detection means for detecting a component of an associated interrogating light beam passing through said first polarizing means, said flow channel and said second polarizing means, wherein a birefringent crystalline material in the test sample flowing through said flow channel causes said light beam to include said light beam component, thereby allowing said light beam component to impinge said detection means and signal the presence of said birefringent crystalline material in concentrations representative of in vivo conditions.

2. The microcrystal detection apparatus recited in claim 1 further comprising a collector lens for directing said light beam into said second polarizing means.

3. The microcrystal detection apparatus recited in claim 2 wherein said second plane of polarization is rotated 90° relative to said first plane of polarization.

4. The microcrystal detection apparatus recited in claim 3 wherein said flow channel lies orthogonal to said light beam.

5. The microcrystal detection apparatus recited in claim 2 further comprising:
    a focusing lens for focusing said light beam into a focal region;
    said flow channel having inner walls and an inner lateral cross section defined by said inner walls; and
    at least a portion of said inner lateral cross section lying within said focal region.

6. The microcrystal detection apparatus recited in claim 5 wherein said collector lens lies in between said focal region and said second polarizing means.

7. The microcrystal detection apparatus recited in claim 6 wherein said flow channel lies orthogonal to said light beam.

8. The microcrystal detection apparatus recited in claim 7 wherein said second plane of polarization is rotated 90° relative to said first plane of polarization.

9. The microcrystal detection apparatus recited in claim 8 further comprising: said flow channel having a fitting for fluidly communicating with a source of said fluid; and
    a collection reservoir fluidly communicating with said flow channel, for storing said fluid after said fluid has flowed through said flow channel.

10. The microcrystal detection apparatus recited in claim 9 further comprising:
    means for hydrodynamically focusing said fluid flowing through said flow channel into a focal area; and
    said focal area lying within said focal region, whereby said fluid flowing in said flow channel is constricted to flow through said focal region.

11. The microcrystal detection apparatus recited in claim 10 wherein said light beam is emitted by a light source.

12. The microcrystal detection apparatus recited in claim 11 wherein said detection means emits a signal to indicate impingement of said light beam component.

13. The microcrystal detection apparatus recited in claim 12 wherein said signal is an electrical impulse.

14. The microcrystal detection apparatus recited in claim 13 further comprising:
    display means for displaying said signal;
    storage means for storing said signal; and
    interface means for transmitting said signal over a computer network.

15. The microcrystal detection apparatus recited in claim 14 further comprising means for automatically controlling a flow of said fluid from said fluid source into said flow channel.

16. A method for detecting a birefringent microcrystal in a fluid comprising:
    extracting a fluid test sample from a patient;
    flowing the test sample in a flow channel while the test sample remains at substantially the same temperature as when extracted;
    polarizing an interrogating light beam into a first plane of polarization;
    subsequently directing said light beam through said flowing test sample; and
    detecting whether said light beam, after having passed through said test sample, includes a second plane of polarization that is rotated relative to said first plane of polarization, whereby detection of the second plane indicates the presence of the birefringent microcrystal in the test sample in concentrations representative of in vivo conditions.

17. The microcrystal detection method set forth in claim 16 wherein said detecting step includes directing said light beam through a polarizer that passes light having said second plane of polarization.

18. The microcrystal detection method set forth in claim 17 wherein said second plane of polarization is rotated 90° relative to said first plane of polarization.

19. The microcrystal detection method set forth in claim 18 further comprising, after said light beam passes through said fluid, directing said light beam through a collector lens for relaying said light beam to said polarizer.

20. The microcrystal detection method set forth in claim 19 wherein said fluid is flowing in a direction.

21. The microcrystal detection method set forth in claim 20 further comprising orienting said light beam orthogonal to said direction.

22. The microcrystal detection method set forth in claim 21 further comprising:

said light beam through a first lens for focusing said light beam into a focal region; and flowing said fluid through a transparent flow channel having inner walls and an inner lateral cross section defined by said inner walls; wherein at least a portion of said inner lateral cross section lies within said focal region.

23. The microcrystal detection method set forth in claim 22 further comprising emitting a signal when said second plane of polarization is detected as being included within said light beam.

24. The microcrystal detection method set forth in claim 23 further comprising:

visually displaying said signal;

storing said signal; and said signal over a computer network.

25. The microcrystal detection method set forth in claim 24 further comprising hydrodynamically focusing said fluid flowing through said flow channel into a focal area lying within said focal region.

26. The microcrystal detection method set forth in claim 25 further comprising forcing said fluid to flow from a source of said fluid, through said flow channel, and into a collection reservoir.

27. The microcrystal detection method set forth in claim 26 further comprising, when said light beam includes said second plane of polarization, relaying said light beam from said polarizer to an electronic photo-detector.

28. The microcrystal detection method set forth in claim 16:

wherein the test sample is flowed in the flow channel without delay after extraction from the patient, whereby the test sample remains at substantially the same temperature at detection as at extraction.

29. The microcrystal detection method set forth in claim 28:

wherein the test sample is flowed in the flow channel immediately after extraction from the patient, whereby the test sample remains at substantially the same temperature at detection as at extraction.

* * * * *